(12) United States Patent
Mahfouz et al.

(10) Patent No.: US 8,231,634 B2
(45) Date of Patent: Jul. 31, 2012

(54) METHODS OF PREDETERMINING THE CONTOUR OF A RESECTED BONE SURFACE AND ASSESSING THE FIT OF A PROSTHESIS ON THE BONE

(75) Inventors: Mohamed Mahfouz, Knoxville, TN (US); Brian D. Earl, South Bend, IN (US)

(73) Assignee: Zimmer, Inc., Warsaw, IN (US)

( * ) Notice: Subject to any disclaimer, the term of this patent is extended or adjusted under 35 U.S.C. 154(b) by 1521 days.

(21) Appl. No.: 11/685,906

(22) Filed: Mar. 14, 2007

(65) Prior Publication Data

US 2007/0255288 A1    Nov. 1, 2007

Related U.S. Application Data

(60) Provisional application No. 60/783,630, filed on Mar. 17, 2006.

(51) Int. Cl.
  *A61B 17/60* (2006.01)
  *A61F 2/00* (2006.01)
(52) U.S. Cl. ................................................ 606/102
(58) Field of Classification Search ............ 606/53, 606/86 R, 102
  See application file for complete search history.

(56) References Cited

U.S. PATENT DOCUMENTS

| | | | |
|---|---|---|---|
| 4,549,540 A | 10/1985 | Caspari et al. |
| 4,913,413 A | 4/1990 | Raab |
| 4,936,862 A | 6/1990 | Walker et al. |
| 5,030,237 A | 7/1991 | Sorbie et al. |
| 5,403,319 A | 4/1995 | Matsen, III et al. |
| 5,408,409 A | 4/1995 | Glassman et al. |
| 5,540,696 A | 7/1996 | Booth, Jr. et al. |
| 5,682,886 A | 11/1997 | Delp et al. |
| 5,792,147 A | 8/1998 | Evans et al. |
| 5,828,813 A | 10/1998 | Ohm |
| 5,834,759 A | 11/1998 | Glossop |
| 5,871,018 A | 2/1999 | Delp et al. |
| 5,921,992 A | 7/1999 | Costales et al. |
| 6,006,126 A | 12/1999 | Cosman |
| 6,096,050 A | 8/2000 | Audette |
| 6,160,264 A | 12/2000 | Rebiere |
| 6,197,017 B1 | 3/2001 | Brock et al. |
| 6,205,411 B1 | 3/2001 | DiGioia, III et al. |
| 6,233,504 B1 | 5/2001 | Das et al. |
| 6,338,716 B1 | 1/2002 | Hossack et al. |
| 6,348,058 B1 | 2/2002 | Melkent et al. |

(Continued)

FOREIGN PATENT DOCUMENTS

DE    2821247 A1    11/1979

(Continued)

OTHER PUBLICATIONS

Viceconti, Marco, et al., An automated method to position prosthetic components within multiple anatomical spaces, Computer Methods and Programs in Biomedicine, 2003, 121-127, V.70 No. 2, Istituti Ortopedici Rizzoli, Bologna, Italy.

(Continued)

*Primary Examiner* — Anu Ramana
(74) *Attorney, Agent, or Firm* — Faegre Baker Daniels

(57) ABSTRACT

Methods for predetermining a contour of a resected bone surface and assessing a fit of a prosthesis on the resected bone surface, for designing prostheses to fit discrete patient populations, and for designing customized prostheses.

19 Claims, 4 Drawing Sheets

U.S. PATENT DOCUMENTS

| | | |
|---|---|---|
| 6,430,434 B1 | 8/2002 | Mittelstadt |
| 6,434,507 B1 | 8/2002 | Clayton et al. |
| 6,450,978 B1 | 9/2002 | Brosseau et al. |
| 6,470,207 B1 | 10/2002 | Simon et al. |
| 6,490,467 B1 | 12/2002 | Bucholz et al. |
| 6,490,475 B1 | 12/2002 | Seeley et al. |
| 6,491,699 B1 | 12/2002 | Henderson et al. |
| 6,510,334 B1 | 1/2003 | Schuster et al. |
| 6,533,737 B1 | 3/2003 | Brosseau et al. |
| 6,697,664 B2 | 2/2004 | Kienzle III et al. |
| 6,701,174 B1 | 3/2004 | Krause et al. |
| 6,772,026 B2 | 8/2004 | Bradbury et al. |
| 6,932,842 B1 | 8/2005 | Litschko et al. |
| 7,024,032 B2 | 4/2006 | Kidd et al. |
| 7,029,477 B2 | 4/2006 | Grimm |
| 7,039,225 B2 | 5/2006 | Tanaka et al. |
| 7,194,295 B2 | 3/2007 | Vilsmeier |
| 7,234,937 B2 | 6/2007 | Sachdeva et al. |
| 7,242,999 B2 | 7/2007 | Wang |
| 7,275,023 B2 | 9/2007 | Chen et al. |
| 7,587,075 B1 | 9/2009 | Stefan et al. |
| 7,634,306 B2 | 12/2009 | Sarin et al. |
| 7,646,901 B2 | 1/2010 | Murphy et al. |
| 2002/0068942 A1 | 6/2002 | Neubauer et al. |
| 2003/0033127 A1 | 2/2003 | Lett |
| 2003/0130665 A1 | 7/2003 | Pinczewski et al. |
| 2003/0225415 A1 | 12/2003 | Richard |
| 2004/0102866 A1 | 5/2004 | Harris et al. |
| 2004/0111183 A1 | 6/2004 | Sutherland et al. |
| 2004/0122305 A1 | 6/2004 | Grimm et al. |
| 2004/0146830 A1 | 7/2004 | Weinstein |
| 2004/0152955 A1 | 8/2004 | McGinley et al. |
| 2004/0153062 A1 | 8/2004 | McGinley et al. |
| 2004/0204760 A1* | 10/2004 | Fitz et al. .................. 623/14.12 |
| 2004/0230199 A1 | 11/2004 | Jansen et al. |
| 2004/0236424 A1* | 11/2004 | Berez et al. ................ 623/14.12 |
| 2005/0076521 A1 | 4/2005 | Said |
| 2005/0119564 A1 | 6/2005 | Rosholm et al. |
| 2005/0197814 A1 | 9/2005 | Aram et al. |
| 2005/0198849 A1 | 9/2005 | Goeggelmann et al. |
| 2005/0234332 A1 | 10/2005 | Murphy |
| 2006/0094951 A1 | 5/2006 | Dean et al. |
| 2006/0100498 A1 | 5/2006 | Boyce et al. |
| 2006/0100832 A1 | 5/2006 | Bowman |
| 2006/0161051 A1 | 7/2006 | Terrill-Grisoni et al. |
| 2006/0204067 A1 | 9/2006 | Tuma et al. |
| 2006/0216681 A1 | 9/2006 | Walker et al. |
| 2006/0229624 A1 | 10/2006 | May et al. |
| 2007/0066893 A1 | 3/2007 | Eriksen et al. |
| 2007/0066917 A1 | 3/2007 | Hodorek et al. |
| 2007/0123894 A1 | 5/2007 | Claypool et al. |
| 2007/0156066 A1 | 7/2007 | McGinley et al. |
| 2007/0156157 A1 | 7/2007 | Nahum et al. |
| 2007/0203605 A1 | 8/2007 | Melton et al. |
| 2007/0255288 A1 | 11/2007 | Mahfouz et al. |
| 2007/0274442 A1 | 11/2007 | Gregory et al. |
| 2008/0163344 A1 | 7/2008 | Yang |
| 2008/0167547 A1 | 7/2008 | Bova et al. |
| 2009/0048597 A1 | 2/2009 | Heavener et al. |
| 2009/0089034 A1 | 4/2009 | Penney et al. |

FOREIGN PATENT DOCUMENTS

| | | |
|---|---|---|
| EP | 1403203 A2 | 4/2004 |
| FR | 2776176 A2 | 3/1998 |
| WO | WO99/37220 A1 | 7/1999 |
| WO | WO00/03210 A1 | 1/2000 |
| WO | WO03/030738 A1 | 4/2003 |
| WO | WO2004/017842 A2 | 3/2004 |
| WO | WO2004/019792 A1 | 3/2004 |
| WO | WO94/23605 A1 | 10/2004 |

OTHER PUBLICATIONS

Testi, Debora, et al., JIDE: a new software for computer-aided design of hip prosthesis, Computer Methods and Programs in Biomedicine, 2004, 213-220, V.75 No. 3, Istituti Ortopedici Rizzoli, Bologna, Italy.

Viceconti, Marco, et al., TRI2SOLIDE: an application of reverse engineering methods to the creation of Cad models of bone segments, Computer Methods and Programs in Biomedicine, 1998, 211-220, V.56 No. 3, Istituti Ortopedici Rizzoli, Bologna, Italy.

International Search Report and Written Opinion mailed in related International Application No. PCT/US2007/063949 on Jul. 27, 2007.

Surgical Technique—Nexgen Complete Knee Solution for the Legacy Knee LPS-Flex Fixed Bearing Knee, Zimmer.

Minimally Invasive Surgical Technique (MIS), Intramedullary Surgical Approach, MIS, the M/G Unicompartmental Knee, Zimmer.

Taylor et al. Robotic Hip Replacement Surgery in Dogs, Medical Applications of Robotics, IEEE Engineering in Medicine & Biology Society 11th Annual International Conference, 1989.

Article Biomedizinische Technik Band 48, Heft 12/2003 "Usability of an Image Based Navigation System in Reconstruction of Leg Alignment in Total Knee Arthroplasty—Results of a Prospective Study," Perlick et al, pp. 339-343.

Article the Journal of Arthroplasty vol. 16, No. 5 (2001) "The Effect of Surgeon Experience on Component Positioning in 673 Press Fit Condylar Posterior Cruciate—Sacrificing Totla Knee Arthroplasties," Mahaluxmivala et al., pp. 635-340.

Article Acta Orthop Scand 2004: 75, "Navigation in Total Knee Arthroplasty CT-Based Implantation Compared With the Conventional Technique," Perlick et al., pp. 464-470.

Kienzle et al "Total Knee Replacement" IEEE Engineering in Medicine and Biology Magazine, IEEE Inc. New York, vol. 14, No. 3, May 1, 1995, p. 301-306.

Office Action mailed Jul. 2, 2010 from the European Patent Office in related European Patent Application No. 07758498.5.

International Preliminary Report on Patentability issued Sep. 23, 2008 in related International Patent Application No. PCT/US2007/063949.

P. "Closed-form solution of absolute orientation using unit quaternions" Berthold K. P. Horn, Reprinted from Journal of the Optical Society of America A. vol. 4, p. 629, Apr. 1987 Optical Society of America, pp. 629-642.

"Point Cloud to CAD Model Registration Methods in Manufacturing Inspection" Tucker et al. Journal of Computing and Information Science in Engineering Technology Review, vol. 6, Dec. 2006.

Biomet Orthopedics, Inc., Signature Personalized Arthritis Care, Sep. 2008.

Biomet Orthopedics, Inc. Product Detail Signature Personalized Patient Care, Sep. 2008.

* cited by examiner

METHODS OF PREDETERMINING THE CONTOUR OF A RESECTED BONE SURFACE AND ASSESSING THE FIT OF A PROSTHESIS ON THE BONE

CROSS REFERENCE TO RELATED APPLICATIONS

This application claims the benefit under Title 35, U.S.C. §119(e) of U.S. Provisional Patent Application Ser. No. 60/783,630, entitled METHODS OF PREDETERMINING THE CONTOUR OF A RESECTED BONE AND THE FIT OF AN IMPLANT ON THE BONE, filed Mar. 17, 2006, the disclosure of which is hereby expressly incorporated herein by reference.

BACKGROUND

The present disclosure relates to methods for determining an optimal fit of a prosthesis on a resected bone surface.

Orthopaedic procedures for the replacement of all, or a portion of, a patient's joint typically require resecting and reshaping of the bones of the joint to receive prosthetic components. For example, a typical total knee prosthesis has three main components: a femoral component for replacing at least a portion of the distal end of the femur, a tibial component for replacing at least a portion of the proximal end of the tibia, and a bearing insert for replacing at least a portion of the articulating tissue between the femur and the tibia. Procedures for implanting a total knee prosthesis typically involve preparing and reshaping both the distal end of the femur and the proximal end of the tibia prior to implanting the prosthetic components. The amount of bone removed may be partially determined by the size and type of prosthetic components to be implanted. The size of prosthetic components may be initially determined by measurements taken of the knee prior to and during surgery, and the final determination of size may be made after taking measurements and trialing a provisional prosthesis during the procedure.

SUMMARY

The present disclosure provides methods for predetermining a contour of a resected bone surface and assessing a fit of a prosthesis on the resected bone surface. The present disclosure also provides methods for designing prostheses to fit discrete patient populations as well as methods for designing customized prostheses.

In one form thereof, the present disclosure provides a method of virtually assessing the fit of a prosthesis for placement on a resected bone surface, the method including the steps of creating a two-dimensional outline of the resected bone surface; creating a two-dimensional outline of a first prosthesis; and comparing the two-dimensional outline of the resected bone surface with the two-dimensional outline of the first prosthesis.

In another form thereof, the present disclosure provides an apparatus for virtually assessing the fit of a prosthesis for placement on a resected bone surface, the apparatus including a first computer adapted to create a two-dimensional outline of the resected bone surface; a second computer for creating a two-dimensional outline of a first prosthesis; and a third computer for comparing the two-dimensional outline of the resected bone surface with the two-dimensional outline of the first prosthesis.

In yet another form thereof, the present disclosure provides a method of designing a prosthesis to substantially fit a resected bone surface based on a population of bones, the method including the steps of creating a plurality of two-dimensional outlines corresponding to each resected bone surface for each bone of the population; and determining a contour of a bone engaging surface of a prosthesis using the plurality of two-dimensional outlines, wherein the contour substantially matches the plurality of two-dimensional outlines of the resected bone surfaces.

In still another form thereof, the present disclosure provides an apparatus for designing a prosthesis to substantially fit a resected bone surface based on a population of bones, the apparatus including a first computer for creating a plurality of two-dimensional outlines corresponding to each resected bone surface for each bone of the population; and a second computer for determining a contour of a bone engaging surface of a prosthesis which substantially matches the plurality of two-dimensional outlines of the resected bone surfaces.

In one form thereof, the present disclosure provides a method of creating a prosthesis for placement on a resected bone surface, the method including the steps of creating a two-dimensional outline of the resected bone surface; and determining a contour of a bone engaging surface of a prosthesis using the two-dimensional outline of the resected bone surface.

In another form thereof, the present disclosure provides an apparatus for creating a prosthesis for placement on a resected bone surface, the apparatus including a first computer for creating a two-dimensional outline of the resected bone surface; and a second computer for determining a contour of a bone engaging surface of a prosthesis using the two-dimensional outline of the resected bone surface.

BRIEF DESCRIPTION OF THE DRAWINGS

The above mentioned and other features of the disclosure, and the manner of attaining them, will become more apparent and will be better understood by reference to the following description of embodiments of the disclosure taken in conjunction with the accompanying drawings, wherein.

Figure 1:
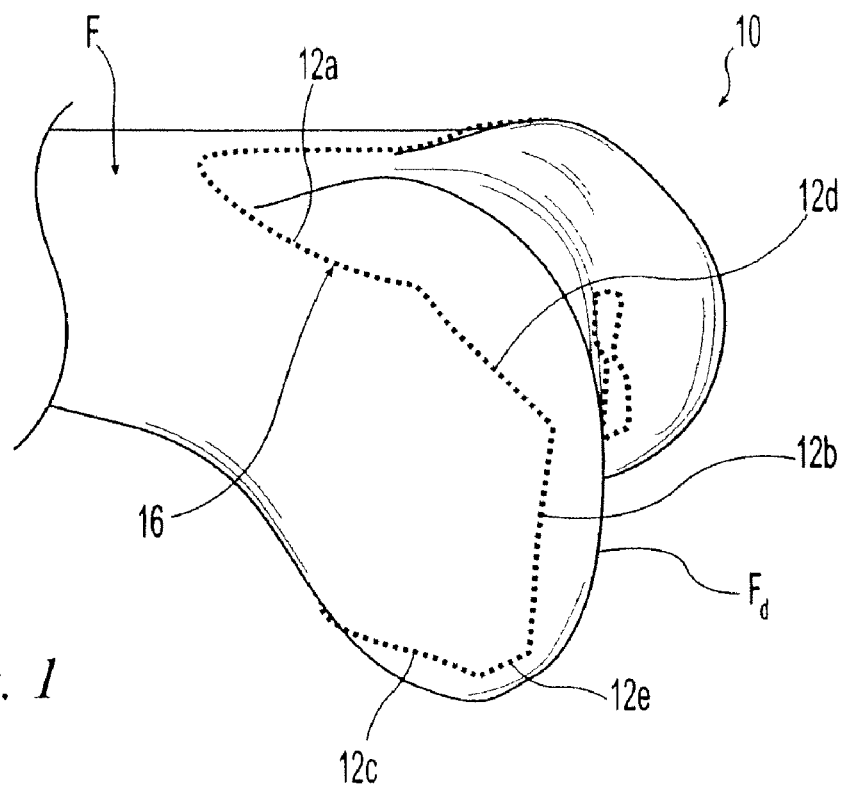
FIG. 1 is a perspective view of a digital model of the distal end of a femur including a virtual resection according to an exemplary method of the present disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure. Although the exemplifications set out herein illustrate embodiments of the disclosure, the embodiments disclosed below are not intended to be exhaustive or to be construed as limiting the scope of the invention to the precise forms disclosed.

DETAILED DESCRIPTION

The present disclosure may include references to the following terms: anterior (at or near the front of the body, as opposed to the back of the body); posterior (at or near the back of the body, as opposed to the front of the body); lateral (at or near the side of the body, farther from the midsagittal plane, as opposed to medial); medial (at or near the middle of the body, at or near the midsagittal plane, as opposed to lateral); proximal (toward the beginning, at or near the head of the body, as opposed to distal); and distal (further from the beginning, at or near the foot of the body, as opposed to proximal).

Referring to FIGS. 1-8, an exemplary method of the present disclosure may be used to determine how a femoral prosthesis will fit on the distal end of a femur, i.e., to assess whether a prosthesis is of the right size and shape for the distal end of the femur and whether the prosthesis suitably conforms thereto. The method generally includes the steps of obtaining a three-dimensional (3-D) model of a bone based on an acquired image of the bone, virtually resecting the 3-D model of the bone, i.e., creating or simulating a resection of the bone within a computer or other intelligent processing device, preparing a bone profile of the virtual resection, creating a two-dimensional (2-D) outline or footprint of the resection from the bone profile, preparing a prosthesis profile, creating a 2-D outline or footprint from the prosthesis profile, and comparing the 2-D outlines of the bone profile and the prosthesis profile to assess or determine the fit of the prosthesis with the bone.

More particularly, referring to FIG. 1, 3-D digital model 10 of an exemplary femur F is illustrated. Digital model 10 may be obtained by obtaining a computed tomography ("CT") scan of a femur to produce a 3-D image of the femur and converting the 3-D image to digital model 10. The conversion of the 3-D CT scan image to 3-D digital model 10 may be performed using any suitable modeling software including, for example, Amira®, available from Mercury Computer Systems, Inc., of Chelmsford, Mass. Digital model 10 may include femur F having distal end $F_d$.

Figure 2:
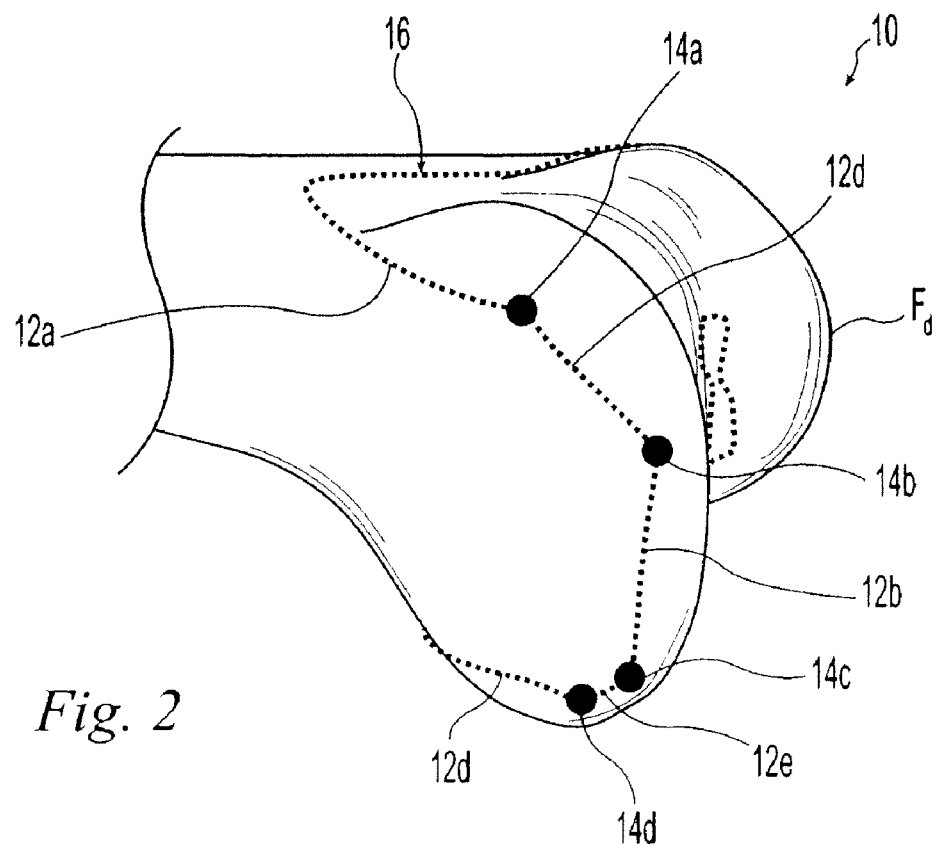
FIG. 2 is a perspective view of the digital model of FIG. 1, further illustrating the vertices of the virtual resection.
Figure 3:
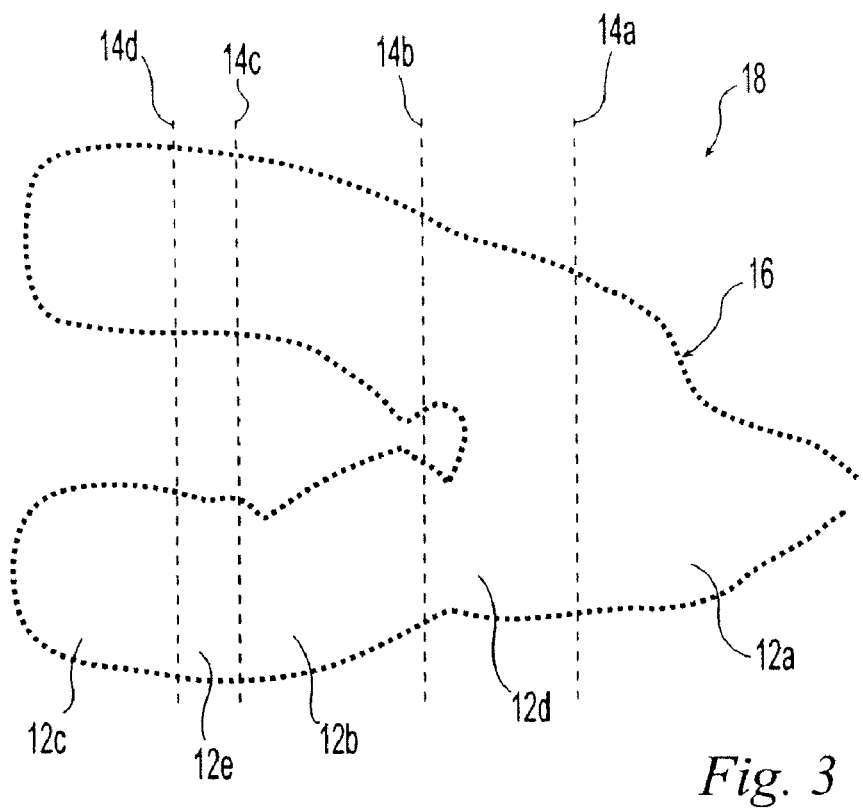
FIG. 3 is a top view of the two-dimensional outline of the femoral resection of FIG. 1.
Figure 4:
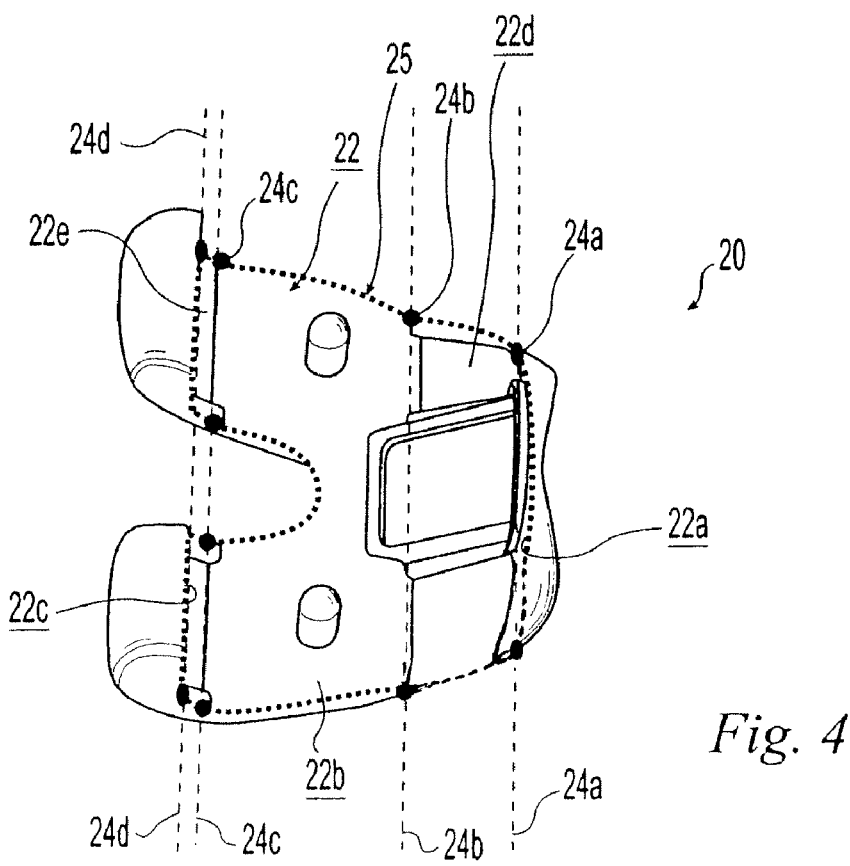
FIG. 4 a perspective view of an exemplary distal femoral prosthesis which may be used in an exemplary method of the present disclosure.

Referring still to FIG. 1, using suitable software, such as MATLAB®, available from The MathWorks, of Natick, Mass., and Unigraphics®, available from UGS Corp., of Plano, Tex., a virtual resection of distal end $F_d$ of model femur F is performed. Similar to the resection performed in actual knee arthroplasty procedures, the virtual resection involves defining femoral cut planes 12a-12e on distal end $F_d$ of model femur F. Femoral cut planes 12a-12e are calculated using an algorithm of the software. The algorithm calculates femoral cut planes 12a-12e based on a proposed, exemplary femoral prosthesis and the known surgical technique specified for the proposed femoral prosthesis. More particularly, distal end $F_d$ of model femur F may be preliminarily measured based on the known surgical technique and using the software described above. The resulting measurements are used to preliminarily select a femoral prosthesis size and type. Resection of distal end $F_d$ of model femur F is determined by the selected femoral prosthesis and involves resecting distal end $F_d$ of femur F to complement and receive the prosthesis. For example, as shown in FIG. 4, model femoral prosthesis 20 may be preliminarily selected. Femoral prosthesis 20 is a cruciate-retaining femoral prosthetic component having bone engaging surface 22. Bone engaging surface 22 includes a plurality of intersecting planar surfaces, including anterior surface 22a, distal surface 22b, posterior surface 22c, anterior chamfer surface 22d, and posterior chamfer surface 22e. Accordingly, as shown in FIG. 1, the virtual resection of distal end $F_d$ of model femur F includes defining a plurality of intersecting cut planes 12a-12e including anterior cut plane 12a, distal cut plane 12b, posterior cut plane 12c, anterior chamfer cut plane 12d, and posterior chamfer cut plane 12e, which correspond to the plurality of intersecting planar surfaces 22a-22e of model prosthesis 20 (FIG. 4). As illustrated in FIGS. 2 and 3, cut planes 12a-12e intersect one another at femoral cut plane vertices 14a-14d. More particularly, anterior cut plane 12a intersects anterior chamfer cut plane 12d at vertex 14a. Anterior chamfer cut plane 12d intersects distal cut plane 12b at vertex 14b. Distal cut plane 12b intersects posterior chamfer cut plane 12e at vertex 14c. Posterior chamfer cut plane 12e intersects posterior cut plane 12c at vertex 14d.

Referring still to FIGS. 1 and 2, femoral profile 16, shown as a dotted line, of the virtually resected model femur F is prepared by outlining cut planes 12a-12e extending between cut plane vertices 14a-14d. Two-dimensional outline or footprint 18 of the resected surface of model femur F is then obtained, as shown in FIG. 3, by unfolding or bending profile 16 at cut plane vertices 14a-14d until cut planes 12a-12e are aligned in a single plane. The suitable software mentioned above may be used to manipulate profile 16 to create two-dimensional outline 18.

Figure 5:
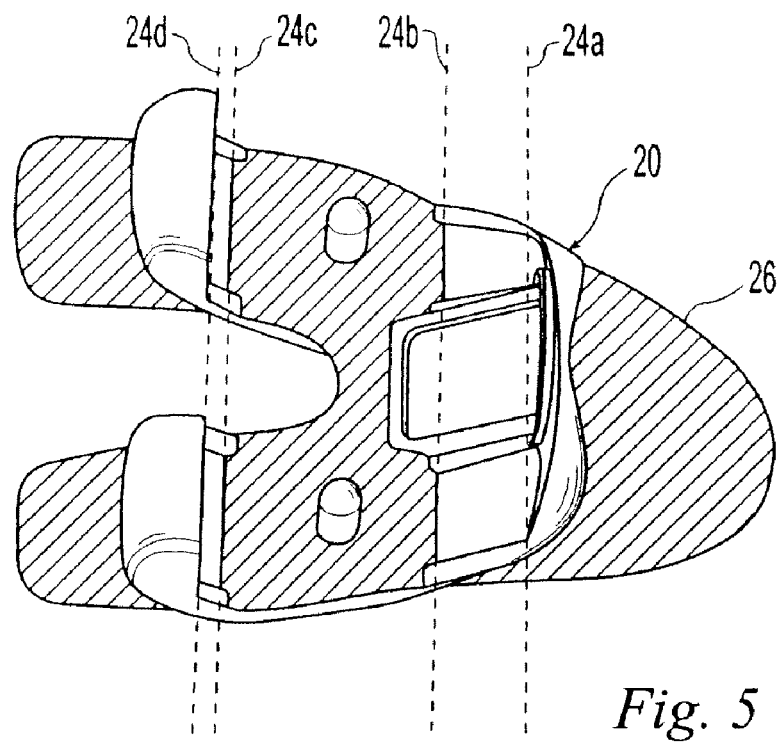
FIG. 5 is a perspective view of the prosthesis of FIG. 4, further illustrating the step of virtually unfolding the prosthesis.
Figure 6:
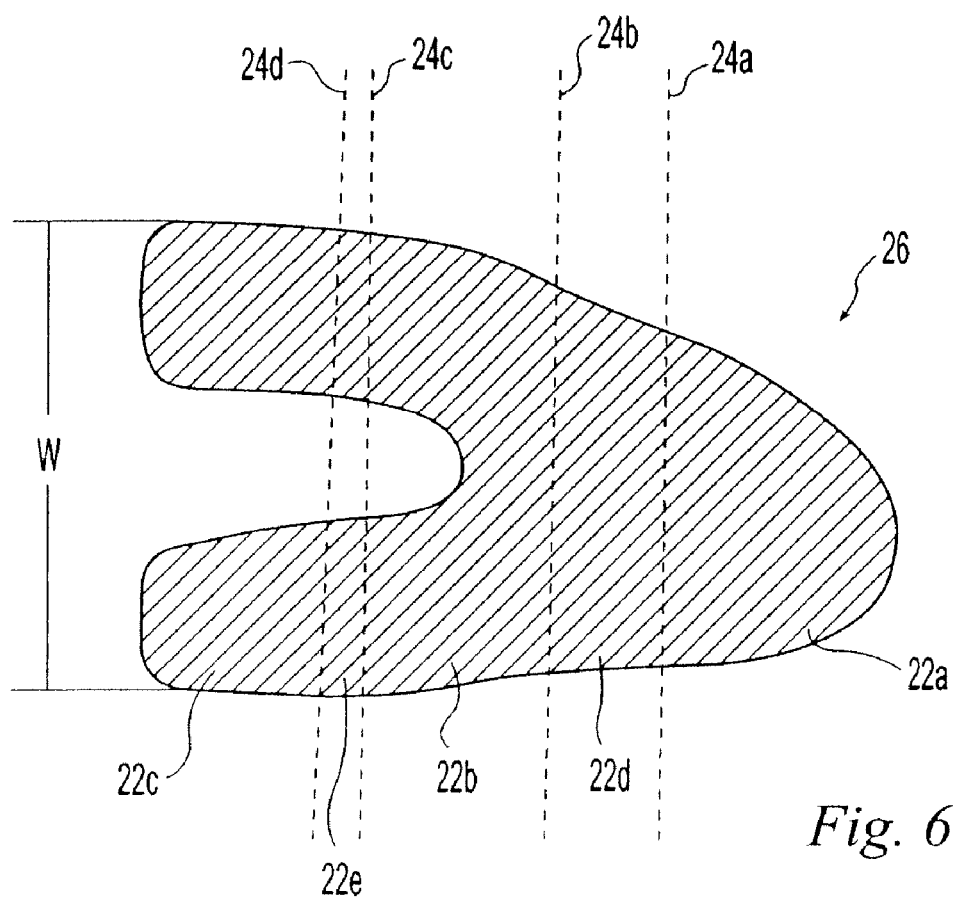
FIG. 6 is a top view of the two-dimensional outline of the prosthesis of FIG. 4 after the unfolding step of FIG. 5.

Referring now to FIGS. 4-6, two-dimensional outline or footprint 26 of proposed prosthesis 20 may be made using a process similar to that described above for outline or footprint 18 of femoral profile 16. More particularly, 3-D digital model 20 of a femoral prosthesis may be obtained using any known method and any suitable software, including those described above. As discussed above, model prosthesis 20 includes bone engaging surface 22, which includes anterior planar surface 22a, distal planar surface 22b, posterior planar surface 22c, anterior chamfer planar surface 22d, and posterior chamfer planar surface 22e. Planar surfaces 22a-22e intersect one another at prosthesis vertices 24a-24d. More particularly, anterior planar surface 22a intersects anterior chamfer surface 22d at vertex 24a. Anterior chamfer surface 22d intersects distal planar surface 22b at vertex 24b. Distal planar surface 22b intersects posterior chamfer surface 22e at vertex 24c, and posterior chamfer surface 22e intersects posterior surface 22c at vertex 24d. Anterior planar surface 22a of prosthesis 20 corresponds to anterior cut plane 12a of femur F; anterior chamfer surface 22d of prosthesis 20 corresponds to anterior chamfer cut plane 12d of femur F; distal planar surface 22b of prosthesis 20 corresponds to distal cut plane 12b of femur F; posterior chamfer surface 22e of prosthesis 20 corresponds to posterior chamfer cut plane 12e of femur F; posterior surface 22c of prosthesis 20 corresponds to posterior cut plane 12c of femur F; vertex 24a of prosthesis 20 corresponds to vertex 14a of femur F; vertex 24b of prosthesis 20 corresponds to vertex 14b of femur F; vertex 24c of prosthesis 20 corresponds to vertex 14c of femur F; and vertex 24d of prosthesis 20 corresponds to vertex 14d of femur F.

Referring to FIG. 4, prosthesis profile 25 of model prosthesis 20 is prepared by outlining the perimeter of intersecting planar surfaces 22a-22e between prosthesis vertices 24a-24d. Prosthesis profile 25 is represented by the heavy dashed line extending about the perimeter of model prosthesis 20. Turning to FIGS. 5 and 6, two-dimensional outline or footprint 26 of prosthesis profile 25 is created by using the suitable software to unfold or bend profile 25 at vertices 24a-24d until planar surfaces 22a-22e are aligned within a single plane.

Prosthesis outline 26 may be visually compared with femur outline 18 to determine and assess whether model prosthesis 20 is a suitable fit for model femur 10. Thus, a surgeon may compare outline 26 with outline 18 and determine whether prosthesis 20 corresponding to outline 26 is an acceptable prosthesis to use for femur F. Prosthesis outline 26 may be compared with femur outline 18 by superimposing one atop the other and observing the overlapping shapes and the differences therebetween. Furthermore, using the suitable software mentioned above, quantitative analysis may be made of outlines 26 and 18. For instance, measurements of outlines 26 and 18 may be taken and the suitable software can calculate deviations between the measurements. For example, width measurements of outlines 26 and 18 at the intersections of each planar surface may be taken and/or at midpoints of each planar surface between such intersections with other planar surfaces. Any deviations between outlines 26 and 18 may then be used to calculate proposed changes in prosthesis 20 to thereby reshape prosthesis 20 to minimize the deviations. Alternatively, any deviations between outlines 26 and 18 may prompt a user to select a different prosthesis 20 and perform the same analysis to assess the fit of the second prosthesis 20 on model femur 10, i.e., if a surgeon decides that outline 26 of a first prosthesis 20 is unacceptable for femur F, then the surgeon then compares the outline 26 of another prosthesis 20 until an acceptable prosthesis is identified.

The method described above has several useful, practical applications. For example, the method described above may be used to develop new and improved existing prosthesis designs. It is contemplated that this method may be used to survey a large population of subjects to develop statistics and identify trends in bone shapes, and to adapt prosthesis sizes and shapes accordingly. More specifically, two-dimensional footprints of virtually resected bones of a large population of patients may be obtained and compared to two-dimensional footprints of numerous available prostheses.

Figure 7:
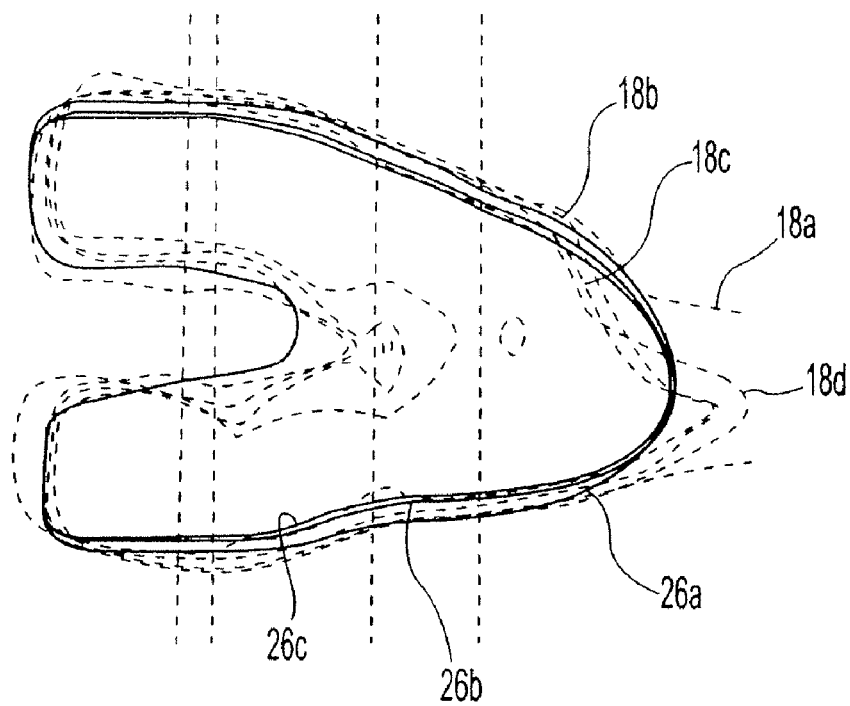
FIG. 7 is an illustration of another step of the method of the present disclosure wherein outlines of several exemplary prostheses are compared with outlines of several virtually resected exemplary femurs.
Figure 8:
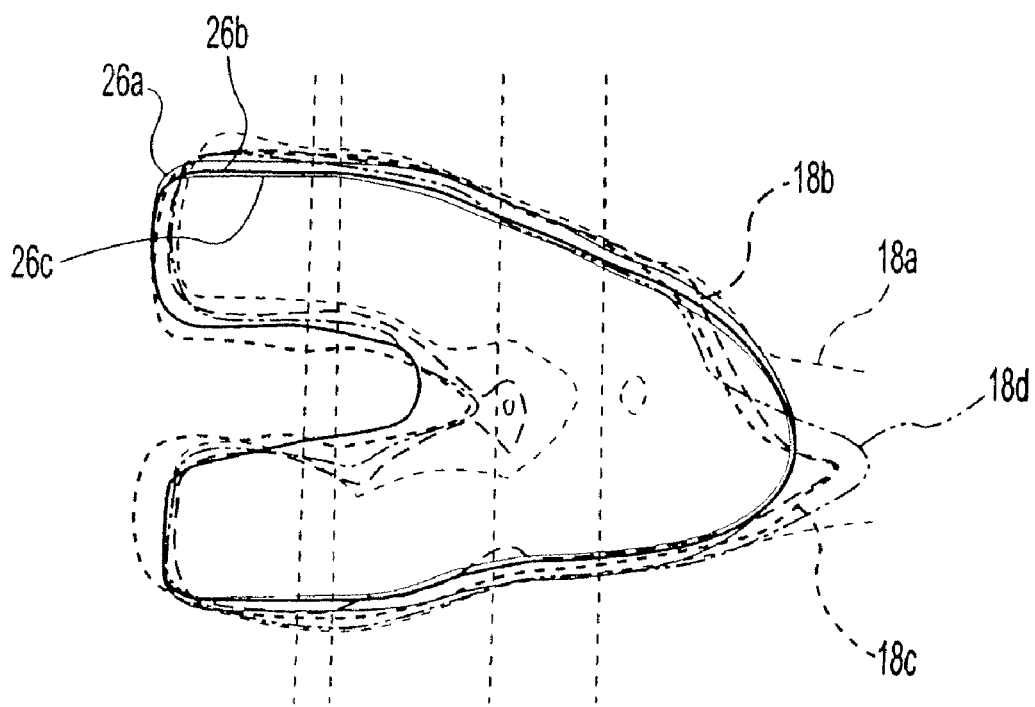
FIG. 8 is another illustration of the step shown in FIG. 7.

FIGS. 7 and 8 illustrate an exemplary application of the methods of the present disclosure. FIG. 7 illustrates femur footprints or outlines 18a-18d, shown as dotted lines, taken from a virtually resected model of a femur of four different subjects compared with footprints or outlines 26a-26c, shown in solid lines, taken from three different models of available prostheses. FIG. 8 illustrates the same footprints 18a-18d, 26a-26c. The comparison shown in FIGS. 7 and 8 demonstrates that the prosthesis yielding footprint 26a is larger in width W (FIG. 6) than the virtually resected bones yielding footprints 18b-18d. In an exemplary embodiment, outlines 18a-18d may be used to design or create a prosthesis which substantially matches at least some of outlines 18a-18d. For example, a prosthesis may be created or designed which is a best fit approximation to a plurality of outlines 18 which may be based on a specific patient population, such as the female population.

In an exemplary embodiment, a method of the present disclosure may be performed on the femurs of a large population of women to obtain medial/lateral and anterior/posterior dimensions of the femurs and calculate ratios between the medial/lateral and anterior/posterior dimensions. These dimensions and calculations may be used in designing femoral components for use on female anatomy. In another exemplary embodiment, a method of the present disclosure may also be used to obtain medial/lateral and anterior/posterior dimensions of existing femoral components and calculate ratios between the medial/lateral and anterior/posterior dimensions of the femoral components. The dimensions and calculated ratios may then be used to compare existing femoral components to the dimensions and calculated ratios of the femurs of women to identify potential areas of the femoral component where fit can be optimized. Such a comparison is fully described in U.S. patent application Ser. No. 11/611,021, entitled DISTAL FEMORAL KNEE PROSTHESES, assigned to the assignee of the present application, the disclosure of which is hereby expressly incorporated herein by reference. The same type of process may be performed for other populations, such as a population of males, various ethnic populations, populations based on age, stature-based populations, and/or populations based on disease progression or disease status.

In addition, the method described above may be used in guiding the design and manufacture of custom prostheses. For instance, a patient's femur may be modeled, virtually resected and footprinted as described above. The footprint could then be used as the footprint for forming a prosthesis.

Although the method described above is exemplified with reference to the distal end of the femur and femoral prostheses, the methods of the present invention may be applied to any bone and any prosthesis.

While this invention has been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method of virtually assessing the fit of a prosthesis for placement on a resected bone surface, the method comprising the steps of:
   obtaining a three-dimensional contour of the resected bone surface;
   creating a two-dimensional outline of the resected bone surface based on the three-dimensional contour of the resected bone surface;
   creating a two-dimensional outline of a first prosthesis; and
   comparing the two-dimensional outline of the resected bone surface with the two-dimensional outline of the first prosthesis.

2. The method of claim 1, further comprising, if said comparing step results in an acceptable match of the outlines, the step of selecting the first prosthesis for physical placement on the resected bone surface.

3. The method of claim 2, further comprising, if said comparing step results in an unacceptable match of the outlines, the steps of creating a two-dimensional outline of a second prosthesis and comparing the two-dimensional outline of the resected bone surface with the two-dimensional outline of the second prosthesis.

4. The method of claim 3, further comprising, if said second comparing step results in an acceptable match of the outline of the resected bone surface and the outline of the second prosthesis, the step of selecting the second prosthesis for physical placement on the resected bone surface.

5. The method of claim 1, wherein said step of creating the two-dimensional outline of the resected bone surface comprises the steps of:
   identifying a vertex of the three-dimensional contour of the resected bone surface between a first planar surface of the resected bone surface and a second planar surface of the resected bone surface;
   manipulating the first planar surface to be coplanar with the second planar surface; and
   outlining a perimeter of the first planar surface and the second planar surface to define the two-dimensional outline of the resected bone surface.

6. The method of claim 1, wherein said step of creating the two-dimensional outline of the first prosthesis comprises the steps of:
   obtaining a three-dimensional contour of the first prosthesis;
   identifying a vertex between a first planar surface of the first prosthesis and a second planar surface of the first prosthesis;
   manipulating the first planar surface to be coplanar with the second planar surface; and
   outlining a perimeter of the first planar surface and the second planar surface to define the two-dimensional outline of the first prosthesis.

7. The method of claim 1, wherein said comparing step comprises superimposing the two-dimensional outline of the resected bone surface on the two-dimensional outline of the first prosthesis.

8. The method of claim 1, wherein the three-dimensional contour of the resected bone surface includes a first planar surface and a second planar surface, the first and second planar surfaces lying in different planes.

9. The method of claim 8, wherein the step of creating the two-dimensional outline of the resected bone surface includes manipulating the first planar surface to be coplanar with the second planar surface.

10. The method of claim 9, wherein the two-dimensional outline of the resected bone surface includes a two-dimensional outline of the first planar surface coplanar with the second planar surface.

11. The method of claim 1, wherein the first prosthesis includes at least one surface configured to be positioned adjacent to the resected bone surface, and wherein the two-dimensional outline of the first prosthesis corresponds to the at least one surface of the first prosthesis.

12. A method of virtually assessing the fit of a prosthesis for placement on a resected bone surface, the method comprising the steps of:
   creating a two-dimensional outline of the resected bone surface;
   creating a two-dimensional outline of a first prosthesis; and
   comparing the two-dimensional outline of the resected bone surface with the two-dimensional outline of the first prosthesis, wherein the resected bone surface includes a first planar surface, a second planar surface, and at least one vertex shared by the first and second planar surfaces, wherein the step of creating the two-dimensional outline of the resected bone surface includes the step of outlining a perimeter of the first and second planar surfaces.

13. A method of virtually assessing the fit of a prosthesis for placement on a resected bone surface, the method comprising the steps of:
   creating a two-dimensional outline of the resected bone surface;
   creating a two-dimensional outline of a first prosthesis; and
   comparing the two-dimensional outline of the resected bone surface with the two-dimensional outline of the first prosthesis, wherein the resected bone surface is defined by a plurality of intersecting cut planes, wherein the step of creating the two-dimensional outline of the resected bone surface includes the step of outlining the plurality of intersecting cut planes to obtain a three-dimensional profile of the resected bone surface, the two-dimensional outline of the resected bone surface being based on the three-dimensional profile of the resected bone surface.

14. The method of claim 13, wherein the step of creating the two-dimensional outline of the resected bone surface includes the step of manipulating the three-dimensional profile of the resected bone surface to form the two-dimensional outline of the resected bone surface.

15. A method of virtually assessing the fit of a prosthesis for placement on a resected bone surface, the method comprising the steps of:
   creating a two-dimensional outline of the resected bone surface;
   creating a two-dimensional outline of a first prosthesis; and
   comparing the two-dimensional outline of the resected bone surface with the two-dimensional outline of the first prosthesis, further including the step of obtaining a three-dimensional contour of a surface of the first prosthesis, the step of creating the two-dimensional outline of the first prosthesis being based on the three-dimensional contour of the surface of the first prosthesis.

16. The method of claim 15, wherein the three-dimensional contour of the first prosthesis includes a first planar surface and a second planar surface, the first and second planar surfaces lying in different planes.

17. The method of claim 16, wherein the step of creating the two-dimensional outline of the first prosthesis includes manipulating the first planar surface to be coplanar with the second planar surface.

18. The method of claim 17, wherein the two-dimensional outline of the first prosthesis includes a two-dimensional outline of the first planar surface coplanar with the second planar surface.

19. A method of virtually assessing the fit of a prosthesis for placement on a resected bone surface, the method comprising the steps of:
   creating a two-dimensional outline of the resected bone surface;
   creating a two-dimensional outline of a first prosthesis; and
   comparing the two-dimensional outline of the resected bone surface with the two-dimensional outline of the first prosthesis, wherein said comparing step comprises the steps of measuring the two-dimensional outline of the resected bone surface and the two-dimensional outline of the first prosthesis and determining a deviation between the two-dimensional outline of the resected bone surface and the two-dimensional outline of the first prosthesis based on the measuring step.

* * * * *